(12) United States Patent
Auxepaules et al.

(10) Patent No.: US 7,833,276 B2
(45) Date of Patent: Nov. 16, 2010

(54) PROSTHETIC ACETABULAR CUP AND PROSTHETIC FEMORAL JOINT INCORPORATING SUCH A CUP

(75) Inventors: Arnaud Auxepaules, Saint-Aubin-sur-Mer (FR); Nicolas Delogé, Douvres (FR); Patrick Raugel, Chargé (FR)

(73) Assignee: Benoist Girard SAS (FR)

( * ) Notice: Subject to any disclaimer, the term of this patent is extended or adjusted under 35 U.S.C. 154(b) by 740 days.

(21) Appl. No.: 10/937,438

(22) Filed: Sep. 9, 2004

(65) Prior Publication Data

US 2005/0060040 A1 Mar. 17, 2005

(30) Foreign Application Priority Data

Sep. 15, 2003 (GB) .................. 0321582.9

(51) Int. Cl.
*A61F 2/32* (2006.01)
(52) U.S. Cl. .................... 623/22.18
(58) Field of Classification Search .... 623/22.11–22.39
See application file for complete search history.

(56) References Cited

U.S. PATENT DOCUMENTS

| | | | | | |
|---|---|---|---|---|---|
| 2,910,978 | A | * | 11/1959 | Urist | 623/22.21 |
| 3,608,096 | A | * | 9/1971 | Link | 23/22.39 |
| 3,903,549 | A | * | 9/1975 | Deyerle | 623/22.36 |
| 4,385,405 | A | * | 5/1983 | Teinturier | 623/22.3 |
| 4,450,592 | A | * | 5/1984 | Niederer et al. | 623/22.21 |
| 4,623,352 | A | * | 11/1986 | Oh | 623/22.28 |
| 4,642,123 | A | * | 2/1987 | Noiles | 623/22.2 |
| 4,662,891 | A | * | 5/1987 | Noiles | 623/22.31 |
| 4,714,477 | A | * | 12/1987 | Fichera et al. | 623/22.19 |
| 4,770,659 | A | * | 9/1988 | Kendall | 623/22.19 |
| 4,795,469 | A | * | 1/1989 | Oh | 623/22.27 |
| 4,822,369 | A | * | 4/1989 | Oueveau et al. | 623/22.14 |
| 4,834,759 | A | * | 5/1989 | Spotorno et al. | 623/22.3 |
| 5,147,407 | A | * | 9/1992 | Tager | 623/22.27 |
| 5,180,394 | A | * | 1/1993 | Davidson | 623/22.15 |
| 5,358,532 | A | * | 10/1994 | Evans et al. | 623/22.23 |
| 5,507,828 | A | * | 4/1996 | Maumy et al. | 623/22.26 |
| 5,609,646 | A | * | 3/1997 | Field et al. | 623/22.32 |
| 5,824,107 | A | * | 10/1998 | Tschirren | 623/22.28 |
| 5,931,870 | A | * | 8/1999 | Cuckler et al. | 623/22.21 |
| 6,413,280 | B1 | | 7/2002 | Feiler | |
| 6,475,243 | B1 | * | 11/2002 | Sheldon et al. | 623/22.28 |
| 6,638,311 | B2 | * | 10/2003 | Wang et al. | 623/22.32 |
| 6,758,864 | B2 | * | 7/2004 | Storer et al. | 623/22.38 |
| 6,811,569 | B1 | * | 11/2004 | Afriat et al. | 623/22.32 |

(Continued)

FOREIGN PATENT DOCUMENTS

DE 4428407 2/1996

(Continued)

*Primary Examiner*—William H. Matthews
*Assistant Examiner*—Ann Schillinger
(74) *Attorney, Agent, or Firm*—Lerner, David, Littenberg, Krumholz & Mentlik, LLP

(57) ABSTRACT

An acetabular prosthesis having an outer member for engaging the acetabulum. The outer member has a part-spherical bearing surface terminating in a distal rim. The rim has a contour such that the portion thereof to be located between the ischium and the pubis extends distally further from an equator of the bearing surface than the contour to be implanted between the pubis and the illium and between the ischium and the illium.

23 Claims, 5 Drawing Sheets

U.S. PATENT DOCUMENTS

| | | | |
|---|---|---|---|
| 6,966,932 B1 * | 11/2005 | Schroeder | 623/22.19 |
| 2002/0116068 A1 * | 8/2002 | McLean | 623/22.15 |
| 2003/0135281 A1 | 7/2003 | Hanssen | |
| 2004/0093090 A1 * | 5/2004 | Barbieri et al. | 623/22.3 |

FOREIGN PATENT DOCUMENTS

| | | |
|---|---|---|
| DE | 19843797 | 3/2000 |
| DE | 19843797 A1 * | 3/2000 |
| EP | 0 552 949 | 7/1993 |
| EP | 0 554 214 | 8/1993 |
| EP | 0 612 509 | 8/1994 |
| EP | 0 681 845 | 11/1995 |
| FR | 2430221 | 2/1980 |
| GB | 2001247 | 1/1979 |
| WO | WO-84/03432 | 9/1984 |
| WO | WO-01/05337 | 1/2001 |
| WO | WO-01/67999 | 9/2001 |
| WO | WO-02/09615 | 2/2002 |

* cited by examiner

PROSTHETIC ACETABULAR CUP AND PROSTHETIC FEMORAL JOINT INCORPORATING SUCH A CUP

BACKGROUND OF THE INVENTION

This invention relates to a prosthetic acetabular cup and to a prosthetic femoral joint incorporating such a cup and comprising a prosthetic femoral stem element which includes a part-spherical bearing head and in which the acetabular cup is adapted to be secured in an acetabulum.

Prosthetic femoral joints of the kind set forth above are well known and the range of angular movement between the bearing head and cooperating acetabular cup is limited by the femoral stem which extends from the bearing head engaging the outer peripheral rim of the cup which is usually in a single plane although in some constructions one side of the peripheral rim may be slightly higher than the other.

The peripheral rim of a natural acetabulum is however contoured in relation to a theoretical plane, for example the proximal shape of the rim is lower between the illium and the pubis, between the pubis and the ischium and between the ischium and the illium. The contour between the pubis and the ischium is lower than the contour between the pubis and illium and between the ischium and the illium. Again, the contours of the rim in a distal direction are higher at the ischium and the illium than the remainder of the rim. Due to the contoured shape the angle of movement at certain positions of the natural femur is greater than that provided by a convention prosthetic femoral joint.

A further difficulty with known prosthetic cups is that if they are not correctly positioned in the acetabulum, or the cup is slightly too large, part of the rim of the cup can be outside the acetabulum in which it is fitted and this can cause the patient pain due to the rim conflicting with the psoas muscle which extends from the acetabulum to the femur, or other muscles or tissues.

SUMMARY OF THE INVENTION

The present invention is intended to provide a prosthetic acetabular cup and a femoral joint incorporating such a cup which provides a more natural angular movement of a femoral stem in the cooperating prosthetic acetabular cup, which decreases the possibility of misalignment of the cup in the acetabulum, and which reduces pain and discomfort for the patient.

According to the present invention a prosthetic acetabular cup for securing in an acetabulum comprises an inner part-spherical bearing surface and an outer peripheral rim portion which is shaped to mimic the contours of the natural shape of an acetabulum.

Thus, due to the shaped contours of the peripheral rim of the acetabular cup, a greater range of motion is provided. Moreover, the contoured shape of the peripheral rim can be used by the surgeon to correctly align the cup in the acetabulum and to ensure that there are no projecting portions which are likely to interfere with the psoas muscle or other muscles and tissues.

It will be appreciated that left or right handed cups are necessary, depending upon which acetabulum they are to be used.

The cup can be of a single or multi-layer construction, composite construction or combination thereof and can include metal and/or synthetic plastics material and preferably the part-spherical bearing surface is made from a synthetic plastics material, for example polyurethane or polyethylene.

The cup can be adapted to be held in the acetabulum by cement, as a press fit or with rigid fixing means, for example, screws, pins or nails.

The metal used in the cup can be monolithic chrome cobalt steel, titanium alloy, stainless steel, or a sandwich construction of any of these materials.

In order to further assist the surgeon in correctly aligning the cup in the acetabulum "landmarks" in the form of markings can be provided, for example, adjacent the illium part of the rim and adjacent the ischium part of the rim.

The invention is particularly, although not exclusively, applicable to prosthetic femoral joints in which the bearing head is of a large diameter approaching or of the same size as a natural femoral head but the cup can be dimensioned to act with a cooperating ball head of any required shape or size.

The invention also includes a prosthetic joint comprising a prosthetic femoral stem element which includes a part-spherical head and a cooperating acetabular cup to accommodate said part-spherical bearing head and which is as set forth above.

In one preferred construction the inner part spherical bearing surface can be arranged to extend around an arc of more than 180° and said bearing head is a snap fit into the bearing insert.

The invention can also be gainfully employed on a unipolar, bipolar or tripolar (dual mobility) type cup. With this arrangement the inner part-spherical bearing surface can be provided on a bearing insert which is freely movable in the cup, and means for retaining the bearing head in freely movable contact with the bearing surface and can also be provided to provide dual mobility of the bearing head in the acetabular cup.

The cup could also have a configuration which includes a part-spherical bearing surface and a substantially cylindrical or conical wall portion, the outer peripheral rim portion of which is shaped to mimic the natural shape of an acetabulum.

If desired, the bearing head can be held in the bearing insert or the cup by an annular retainer when employed in single or double action joint.

In order to place a cup according to the invention which has a bearing surface which extends around an arc of more than 180° or which has a substantially cylindrical or conical wall portion an inserter can be provided which has an annular engagement wall shaped to engage the outer peripheral rim portion of the cup and a resilient annular engagement which can be pushed into the cup under pressure and which resiliently engages the inner wall of the cup adjacent the outer peripheral rim portion.

BRIEF DESCRIPTION OF THE DRAWINGS

The invention can be performed in various ways and some embodiments will now be described by way of example and with reference to the accompanying drawings in which.

DETAILED DESCRIPTION

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Figure 1:
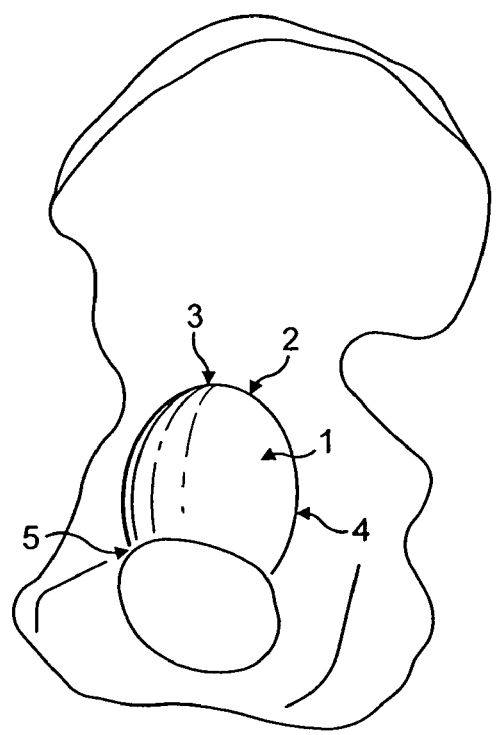
FIG. 1 is a diagrammatic side view of a pelvis showing the acetabulum.

FIG. 1 shows part of a pelvis in which an acetabulum is indicated by reference numeral 1 and which has an outer peripheral wall 2, a pelvis does of course have two acetabulums, right and left, but the construction described below can apply to either of them. The peripheral rim of the outer wall 2 is not symmetrical but has a contoured natural shape. The part of the wall close to the illium is indicated by reference numeral 3, the part of the wall adjacent the ischium is indicated by reference numeral 4 and the part of the wall adjacent the pubis is indicated by reference numeral 5. The peripheral rim varies in contour in relation to a flat plane situation across its face. Thus the part of the rim between the pubis 5 and ischium 4 is lower than the flat plane as is the part of the rim between the ischium 4 and the illium 3. The part of the rim between the pubis 5 and the illium 3 is also slightly lower (more distal). The natural joint takes advantage of the contoured periphery of the right or left acetabulum to allow maximum angular movement of the appropriate femur but in known prosthetic acetabular cups the corresponding peripheral rim is usually in substantially the same plane so that some movement of the joint is lost.

Figure 2:
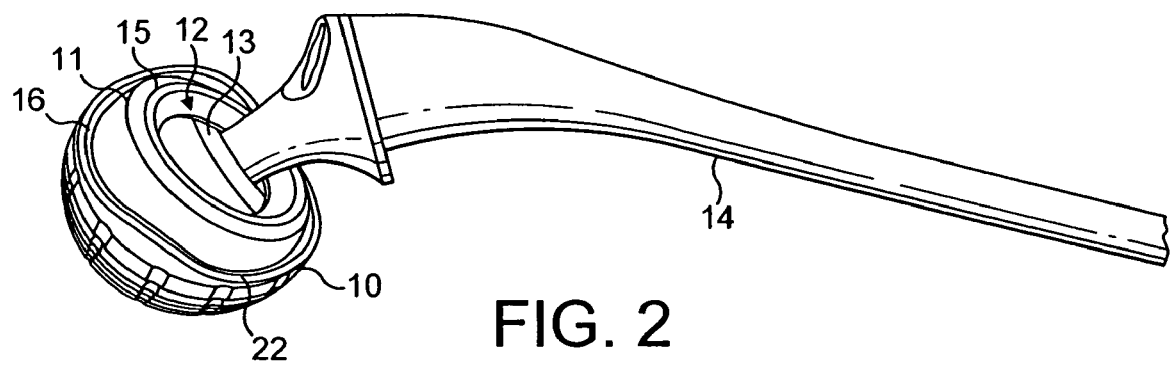
FIG. 2 is an isometric view of a tripolar (dual mobility) prosthetic femoral joint employing a prosthetic acetabular cup according to the invention.

FIG. 2 shows a tripolar (dual mobility) cup of known type but which incorporates the present invention. The cup 10 has a part-spherical bearing insert 11 provided with an inner part-spherical bearing surface 12 which engages a part-spherical bearing head 13 provided on a femoral stem element 14. The bearing insert 11 is freely movable in the inner surface of the cup 10 and means for retaining the bearing head 13 in freely movable contact with the bearing surface 12 is provided by forming the bearing insert 11 from a resilient material, for example, polyurethane or polyethylene, and forming the bearing insert to extend more than 180° around the head 13. The resilience of the resilient material is sufficient to allow the head 13 to be a snap fit into the bearing insert 11. When the stem reaches the position where it engages the end 15 of the bearing insert 11 further movement can be accommodated by allowing the insert 11 to rotate within the cup 10 until the stem 14 reaches the end or rim 16 of the cup.

Dual mobility cups of this type are well known and further angular movement can cause the bearing insert 11 to dislocate from the cup 10. Such dislocation is difficult to control because the insert 11 has to leave the cup 10 to have a dislocation. The dual mobility however presents less wear than single movement systems because the rotation of the insert avoid friction in the same location.

Figure 6:
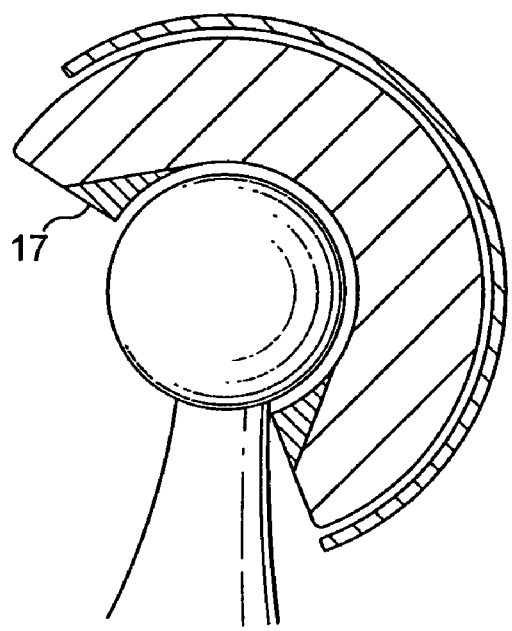
FIG. 6 is a diagrammatic side view of dual mobility femoral cup joint similar to that shown in FIGS. 3, 4 and 5 but using an alternative construction.

FIG. 6 shows a similar construction to FIG. 2 but a retaining ring 17 is provided to locate the bearing head 13 in the insert 11 rather than relying upon a snap fit.

Figure 3:
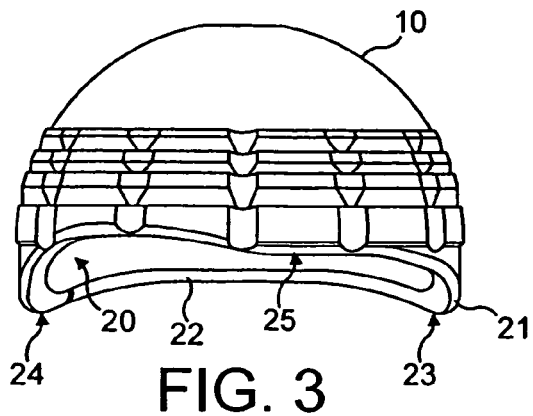
FIG. 3 is a front view of an acetabular cup according to the invention which can be used in the joint shown in FIG. 2.
Figure 4:
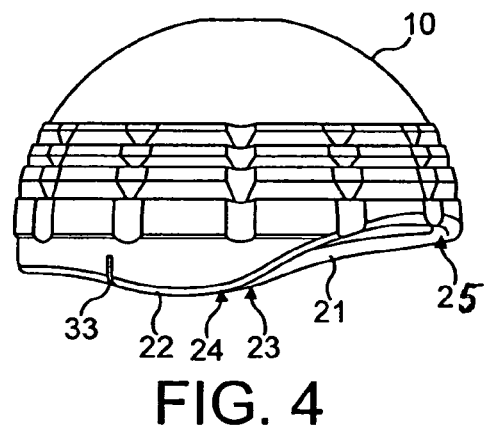
FIG. 4 is an end view of the cup shown in FIG. 3.
Figure 5:
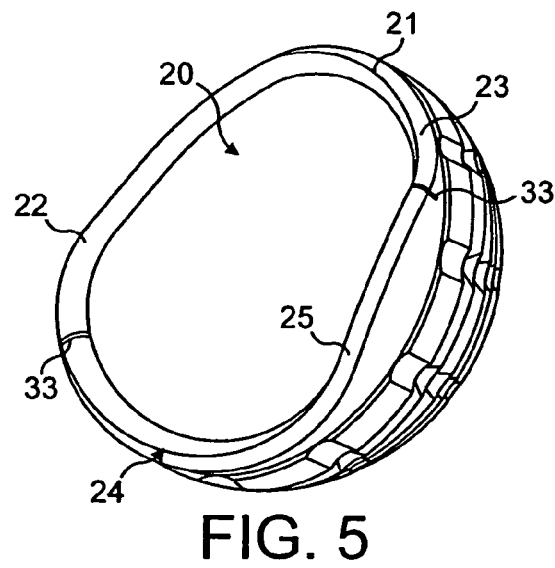
FIG. 5 is an isometric view of the cup shown in FIGS. 3 and 4.

FIGS. 3, 4 and 5 show a construction of a cup 10 according to the present invention which can be used in a dual mobility prosthetic femoral joint as shown in FIG. 2 and which comprises a cup 10 made from a metal or synthetic plastics material, for example, polyethylene or polyurethane. The construction being described, is intended for location in the acetabulum with or without cement. The cup comprises a part-spherical portion extending from an equator 60 to a polar area 62 having an inner bearing surface 20. The lower peripheral edge 21 of the mouth of the cup has an outer peripheral rim portion 22 which is shaped to mimic the contours of the natural shape of the peripheral outer rim of an acetabulum. The part of the spherical rim portion 22 which is intended to be adjacent the pubis 5 is indicated by reference numeral 25. The part of the rim portion 22 which is intended to be adjacent the illium 3 is indicated by reference numeral 23 and the part adjacent the ischium 4 by reference numeral 24. Thus, the peripheral rim portion 22 mimics the contours of the natural shape of the peripheral outer rim of an acetabulum in as much that the part of the rim between the pubis portion 25 and the ischium portion 24 is lower (more distal) than a flat plane as is the part of the rim between the ischium 24 and the illium 23. The part of the rim between the pubis portion 25 and the illium 23 is also slightly lower.

The cup will be contoured appropriately according to whether it is to be used in the right or left acetabulum.

With the peripheral rim contoured as described above the maximum angular movement of the femur can be achieved and little or no movement of the joint is lost.

Figure 7:
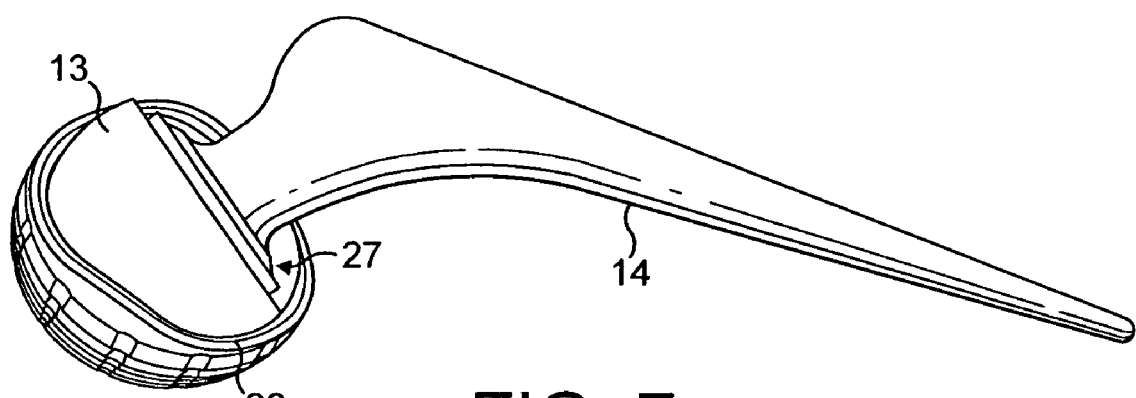
FIG. 7 is an isometric view of a single action prosthetic joint incorporating a cup according to the invention.

The cup of FIGS. 3, 4 and 5 can also be used for use with a part-spherical bearing insert 11 as described with regard to FIGS. 2 to 5 but applied to single action joints. FIG. 7 shows a single action joint incorporating a suitable bearing cup according to the invention. The cup is shown in more detail in FIG. 8. In this figure, the same reference numerals are used to indicate similar parts to those shown in FIGS. 3, 4 and 5 and it will be seen that the peripheral rim portion 22 is contoured in a similar manner. In this construction, however, the cup is provided with a bearing surface 27 which is intended for direct contact with a part-spherical bearing head 13 of a femoral stem element 14. The construction is particularly adaptable for use with a part-spherical bearing head which is of a large diameter approaching or of the same size as the natural femoral head. The cup can be of a single or multi-layer composite construction or a combination thereof and can include metal and/or a synthetic or plastics material and in the construction shown the cup is made from a metal, for example, titanium, and has a synthetic plastics liner 28 on which the bearing surface 27 is provided and made from polyurethane or polyethylene.

As shown in FIG. 7, the cup is of the general external shape shown in FIGS. 3, 4 and 5 and carries projections or inserters to assist in cementing the cup into place or it could be plain.

Figure 8:
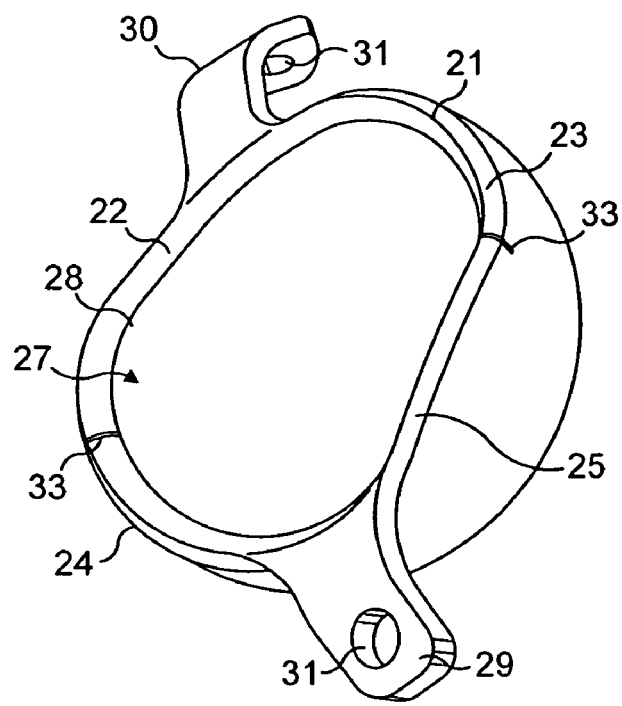
FIG. 8 is an isometric view of an alternative form of cup according to the invention with additional means of fixation for use in a single or double action joint.

If the cup is intended for fixation by means of screws or other mechanical devices, however, the construction could be as shown in FIG. 8 and a pair of lugs 29, 30 can be provided which have openings 31 to accept the fixing means such as screws. The use of lugs 29, 30 is particularly useful for revision surgery applications and such lugs could also be provided on the construction shown in FIGS. 3, 4 and 5.

The part-spherical bearing head 13 can be made of any convenient material, for example, metal in the form of monolithic chrome cobalt alloy, titanium alloy, stainless steel, or a sandwich construction of these materials or it can be made from a ceramics material, for example alumina.

Because of the contoured shape of the peripheral rim portion 22 it is easier for the operating surgeon to correctly position the cup in the acetabulum 1 and ensure that there is no portion of the rim extending outside the acetabulum which could conflict with the psoas muscle or other muscles or tissues.

In order to further assist the surgeon in correctly aligning the cup in the acetabulum "landmarks" in the form of markings 33 can be provided, for example by laser cutting, etching or engraving adjacent the illium part 23 of the rim 22 and adjacent the ischium part 24 of the rim, and will be arranged for use in either the right or left hand acetabulum.

As described above the cup can be substantially hemispherical and can be arranged to extend around an arc of more than 180°, i.e. extend beyond the equator of the cup. Alternatively, it could be hemispherical with a substantially cylindrical or conical wall portion on which the outer peripheral rim portion is formed.

Figure 9:
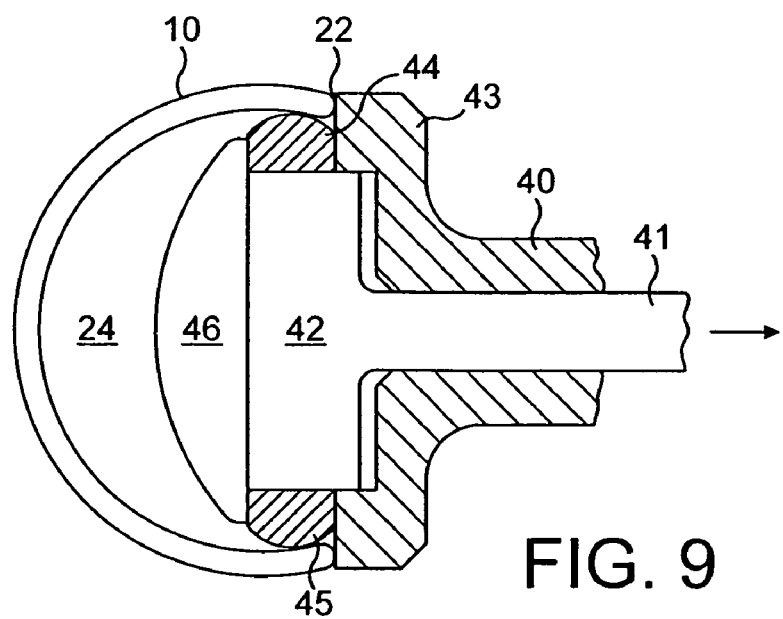
FIG. 9 is a diagrammatic cross-sectional view of an inserter for use with a cup according to the invention.

In order to assist in placing the cup in the acetabulum, an inserter can be provided for use with cups which have a bearing surface which extends around an arc of more than 180° or which has a substantially cylindrical wall portion and such an insert is shown in FIG. 9. The inserter construction comprises a main cylindrical body portion 40 in which is located a push rod 41 provided with an enlarged head 42 with a mushroom shaped top 46. The main body portion has a substantially disc shaped end 43 which provides an annular engagement wall 44 which is shaped to engage the outer peripheral rim portion of the cup 10. As shown in the drawings the bearing surface of the cup extends around an arc of more than 180° and the peripheral rim 22 is as shown in FIGS. 3, 4 and 5. The annular engagement wall 44 is shaped to accommodate the outer peripheral rim of the cup.

The head 4 of the rod 41 carries a resilient annular ring 45 made from resilient material, for example rubber, and located behind the stop 46. The ring 45 is shaped and dimensioned so that it can be pushed into the cup 10 under pressure and will resiliently engage the inner wall 20 of the cup adjacent the outer peripheral rim portion 22 to hold it in place.

All pressure on the cup 10 is accommodated by the engagement of the rim with the wall 44 and when the cup has been placed in position the body portion 40 can slide backwards on the rod 41 and allow the head 42 and engagement ring 45 to be removed.

As described above the inserter is used with a cup which has a bearing surface which extends around an arc of more than 180° but the device can also be used with a cup which comprises a part-spherical bearing surface and a cylindrical extension, the resilient annular engagement ring 45 engaging the cylindrical part of the cup.

Figure 10:
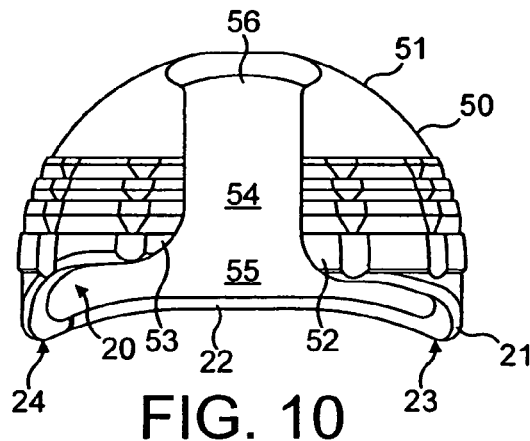
FIG. 10 is a front view of another construction of an acetabular cup according to the invention which can be used in the joint shown in FIG. 2.
Figure 11:
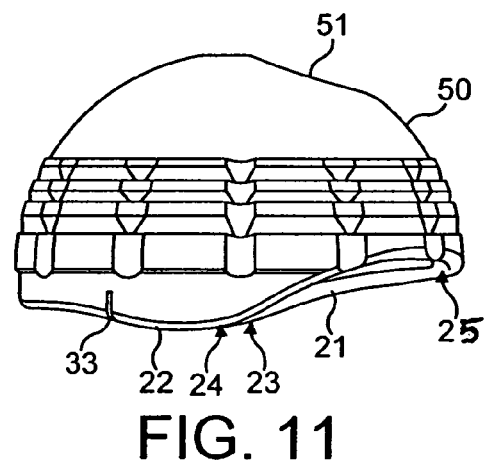
FIG. 11 is an end view of the construction shown in FIG. 10.
Figure 12:
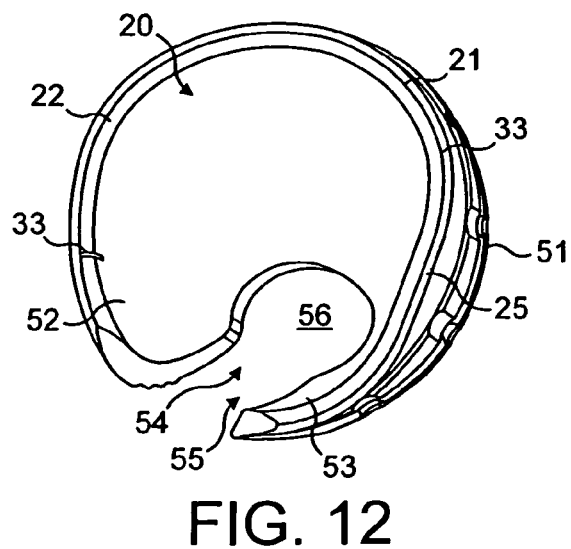
FIG. 12 is an isometric bottom view of the cup shown in FIGS. 10 and 11.

The invention can also be applied to an acetabular cup of the type set forth in U.S. Pat. No. 5,609,646. A cup of this type is shown in FIGS. 10, 11 and 12 and the same reference numerals are used to indicate similar parts. In this construction, however, the cup 50 comprises a part-spherical main portion 51 and two independent arms 52, 53 projecting therefrom and which are separated from each other to provide a gap or opening 54. As will be seen the arms are spaced apart about an arc on the part-spherical main portion 51 breaking out on the rim 22 and the arms themselves and the main portion are together substantially part-spherical. The cup backing thus comprises a substantially part-spherical wall having a rim which is interrupted by a shaped opening to provide the two spaced apart arms 52 and 53.

The main part of the opening 54 is substantially semi-circular and has a mouth 55 which provides the interruption in the rim and which is of smaller width than the remainder 56 of the opening. The backing is therefore substantially horseshoe shaped.

The backing is sufficiently flexible to accept deformation of the acetabulum of the patient but it is usually stiffer than the inner bearing material.

It has been found that this particular shape of opening is convenient and successful and the load is transferred into the pelvis as required. In particular, this shape of opening ensure efficiently that no load is transferred into the bone at undesired locations.

The cup can be for cement or cementless location and all the features as described above and in relation to the previous constructions described can be incorporation. Full details of the construction of this type of cup are set forth in U.S. Pat. No. 5,609,646, the teachings of which are incorporated herein by reference.

From the above description, it will be appreciated that the present invention can provide a prosthetic femoral joint which provides a more natural angular movement of a femoral stem or neck in a cooperating prosthetic acetabular cup and which assists the surgeon in correctly locating the cup in the patient's acetabulum.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic acetabular cup for implantation in an opening of the acetabulum, the acetabulum having a rim extending between the pubis and the ischium through the illium, comprising:
an outer member having an outer surface for engaging and configured to be affixed to the acetabulum, said outer member having a part-spherical inner bearing surface, the outer member extending about a polar axis terminating in a 360° circumferential distal rim surrounding the opening of the acetabulum, the rim having a generally inferiorly facing edge surface, the polar axis is perpendicular to a plane containing the rim of the acetabulum, said generally inferiorly facing edge surface of the rim of the outer member having a contour continuously curved in the generally inferior-superior direction around the entire circumference of the rim with the generally inferiorly facing edge surface moving toward and away from the plane of the acetabular rim two times such that a portion of the generally inferiorly facing edge surface of the rim to be located between the ischium and the pubis extends further towards a polar region of the bearing surface, where the polar axis intersects the bearing surface than a contour portion of the generally inferiorly facing edge surface of the rim to be implanted between the pubis and the illium and a generally inferiorly facing edge surface contour portion to be implanted between the ischium and the illium and a contour portion of the generally inferiorly facing edge surface of the rim to be implanted between the pubis and the illium extends distally further from the polar region than the contour of the generally inferiorly facing edge surface of the rim between the ischium and the illium, wherein the contours of the outer edge of the rim to be implanted at the ischium and the illium are closer to the polar region than the remainder of the rim.

2. The prosthetic acetabular cup as set forth in claim 1 further comprising markings located adjacent the ischium part of the rim.

3. The prosthetic acetabular cup for securing an acetabulum as set forth in claim 1 comprising an inner part-spherical bearing surface and wherein the generally inferiorly facing edge surface is shaped to mimic the contours of the natural shape of an acetabulum.

4. The prosthetic acetabular cup as set forth in claim 3 wherein the cup is of a multi-layer construction, composite construction or combination thereof.

5. The prosthetic acetabular cup as set forth in claim 3 made from metal and/or synthetic plastics material.

6. The prosthetic acetabular cup as set forth in claim 5 wherein the cup is of a two layer sandwich construction.

7. The prosthetic acetabular cup as set forth in claim 5 wherein the metal is monolithic chrome cobalt steel, titanium alloy, stainless steel, or a sandwich construction of any of these materials.

8. The prosthetic acetabular cup as set forth in claim 3 wherein the inner part-spherical bearing surface is made from a synthetic plastics material.

9. The prosthetic acetabular cup as set forth in claim 8 wherein the synthetic plastics material is polyurethane or polyethylene.

10. The prosthetic acetabular cup as set forth in claim 3 wherein the cup is adapted to be held in the acetabulum by cement or a rigid fixing means.

11. The prosthetic acetabular cup as set forth in claim 10 wherein the rigid fixing means are screws, pins or nails.

12. The prosthetic acetabular cup as set forth in claim 3 further comprising acetabulum "landmarks" in the form of markings to assist the surgeon in correctly aligning the cup in an acetabulum in which it is to be used.

13. The prosthetic acetabular cup as set forth in claim 12 wherein the landmarks are located adjacent the illium part of the rim and adjacent the ischium part of the rim.

14. The prosthetic acetabular cup as set forth in claim 3 wherein the cup is dimensioned for use with a bearing head of large diameter approaching or of the same size as a natural femoral head.

15. The prosthetic acetabular cup as set forth in claim 3 which is of the dual mobility type in which the inner part-spherical bearing surface is provided on a bearing insert which is freely movable in the cup.

16. The prosthetic acetabular cup as set forth in claim 15 further comprising means for retaining a bearing head in freely movable contact with the part-spherical bearing surface.

17. The prosthetic acetabular cup as set forth in claim 3 in combination with a cooperating prosthetic femoral stem element which includes a part-spherical head adapted for location therein to form a prosthetic femoral joint.

18. The prosthetic acetabular cup as set forth in claim 17 wherein said bearing surface extends around an arc of more than 180° and said bearing head is a snap fit therein.

19. The prosthetic acetabular cup as set forth in claim 17 wherein said head is held in said bearing surface by an annular retainer.

20. The prosthetic acetabular cup as set forth in claim 17 in which said head is made from a ceramic material.

21. The prosthetic acetabular cup as set forth in claim 20 wherein said head is made from alumina.

22. The prosthetic acetabular cup as set forth in claim 3 in combination with an inserter which includes an annular engagement wall which can engage the outer peripheral rim of the cup, and releasable locating means for resiliently locating the cup adjacent the engagement wall during insertion.

23. The prosthetic acetabular cup as set forth in claim 3 which includes an outer backing and an inner bearing component, said backing comprising a part-spherical main portion and two independent arms projecting therefrom and formed by a separation or opening in the rim of the backing, said backing being made from synthetic plastic material and molded together to form a single component.

* * * * *

UNITED STATES PATENT AND TRADEMARK OFFICE
CERTIFICATE OF CORRECTION

| | |
|---|---|
| PATENT NO. | : 7,833,276 B2 |
| APPLICATION NO. | : 10/937438 |
| DATED | : November 16, 2010 |
| INVENTOR(S) | : Arnaud Aux Epaules et al. |

It is certified that error appears in the above-identified patent and that said Letters Patent is hereby corrected as shown below:

Column 2, line 11, "acetabulum "landmarks" in" should read --acetabulum, "landmarks" in--.
Column 2, line 17, "head but the" should read --head, but the--.
Column 2, line 46, "portion an inserter" should read --portion, an inserter--.
Column 4, line 7, "avoid friction" should read --avoids friction--.
Column 4, line 16, "described, is intended" should read --described is intended--.
Column 5, line 16, "acetabulum "landmarks" in" should read --acetabulum, "landmarks" in--.
Column 6, line 16, "ensure" should read --ensures--.
Column 6, line 61, "surface where" should read --surface, where--.

Signed and Sealed this
Twenty-seventh Day of March, 2012

David J. Kappos
*Director of the United States Patent and Trademark Office*